United States Patent [19]

Kramer

[11] Patent Number: 5,482,056
[45] Date of Patent: Jan. 9, 1996

[54] DETERMINATION OF THUMB POSITION USING MEASUREMENTS OF ABDUCTION AND ROTATION

[76] Inventor: James F. Kramer, P.O. Box 5984, Stanford, Calif. 94309

[21] Appl. No.: 223,284

[22] Filed: Apr. 4, 1994

[51] Int. Cl.$^6$ ............................................ A61B 5/10
[52] U.S. Cl. ............................................ 128/782
[58] Field of Search ............................ 128/774, 782; 338/210

[56] References Cited

U.S. PATENT DOCUMENTS

| | | | |
|---|---|---|---|
| 4,715,235 | 12/1987 | Fukui et al. | 128/782 |
| 4,922,925 | 5/1990 | Crandall et al. | 128/782 |
| 4,988,981 | 1/1991 | Zimmerman et al. | 340/709 |
| 5,047,952 | 9/1991 | Kramer et al. | 364/513.5 |
| 5,086,785 | 2/1992 | Gentile et al. | 128/782 |
| 5,280,265 | 1/1994 | Kramer et al. | 338/210 |
| 5,316,017 | 5/1994 | Edwards et al. | 128/782 |

OTHER PUBLICATIONS

Scott S. Fisher, "Telepresence Master Glove Controller for Dexterous Robotic End–effectors," SPIE vol. 726, Intelligent Robots and Comp. Vis., (1986), pp. 396–401.
Virtual Technologies GyberGlove User's Manual, 2175 Park Blvd., Palo Alto, Calif., 94306, Sep. 24, 1992, pp. 10–17.

*Primary Examiner*—Max Hindenburg

[57] ABSTRACT

Methods and systems are provided for calculating the position of a thumb in a model of links and joints representing the physical thumb. The thumb position and orientation are calculated using the change in values of the angle of the thumb rotation and the thumb abduction from selected initial values, which change is detected by means of sensors mounted in juxtaposition to said thumb. Various joint axes are predefined, while others are calculated.

11 Claims, 6 Drawing Sheets

DETERMINATION OF THUMB POSITION USING MEASUREMENTS OF ABDUCTION AND ROTATION

TECHNICAL FIELD

The field of this invention is the measurement of thumb position.

BACKGROUND

In recent years, the desire to measure hand and finger motion by use of an instrumented glove has become increasingly more popular. Applications which employ such an instrumented glove include: virtual reality, telerobotics, medical hand-function evaluation, music generation, graphical character animation, and the like. One sensing technique which may be used to transduce joint position is a bend sensor, i.e., a sensor which is placed in juxtaposition to a joint and changes its output signal in response to the amount of bending of that joint.

For instrumented glove applications which benefit from knowledge of the position of the various parts of the hand, such as the phalanges of the fingers, in addition to joint angles directly measured, it is desirable to apply the joint angle measurements to a mathematical model of the hand geometry. By applying the measured joint angles to a hand model geometry, and incorporating knowledge of the anatomical structure of the skin and tissue of the hand and thumb, any of a variety of critical points on the hand and thumb at locations not explicitly measured may be calculated.

One desirable application, which makes use of the points on the hand calculated from the hand model, is to render a graphical "virtual" hand on a computer screen which mirrors the position and motion of the physical hand which joints are being sensed. Such a virtual hand may then interact with graphical virtual objects on the computer, where the actions of the virtual hand are controlled by a user's physical hand. Similarly, the points on the hand as calculated from the hand model may also be used to control an anthropomorphic robotic hand, which might be at a nearby or distant location, or located in an undersea or otherwise hazardous environment. Thereby, the robotic hand can be controlled in a human-like fashion by measurements from a physical hand, and where the robotic hand may be used to manipulate heavy or hazardous materials.

To help refer to the various joints and the complex movements of the hand, FIG. 1 is provided, which depicts the anatomical definitions of various joints and bones of the hand. FIG. 6 provides that the instantaneous center of rotation of a physical hand joint is modeled as a hinged joint, where the hinge axis position is constant. In referring to specific joints and links in FIG. 6, it should be understood that the figure is exemplary of typical joint-link constructions of the fingers and hand. Any two joints, such as 600 and 601, may be joined by a link 602, where in certain instances, the link represents one or more physical bone segments 603. Each fingertip 604 is also joined to the nearest joint 600 by a link 605. The angles 606 of joints (e.g., 600) may be measured by goniometers. Using the joint angle information and the kinematic joint-link model of the hand, the position and orientation of various links may be determined. Knowing the position of the bone 603, and using an anatomical model of the bone and surrounding tissue 607 and 608 relative to the link 602, by applying the information to a particular bone of the fingers or hand, we can calculate the position of any point internal to and on the surface 608 of the fingers and hand.

The flexure of the metacarpophalangeal joints, proximal interphalangeal joints and distal interphalangeal joints of the index, middle, ring and small fingers may be modeled in a simple fashion by a single axis of rotation. The metacarpophalangeal joint of each of these four fingers may also be modeled as including an abduction axis which lies normal to the plane defined by the flexure axis and the axis of the metacarpal bone. The flexure of the proximal and distal interphalangeal joints of the thumb may be similarly modeled by a single axis. The articulation of the trapeziometacarpal joint of the thumb (also referred to as the thumb metacarpocarpal joint) is not as simple, and is, in fact, quite complex. By observing the structure of the joint we see it is similar to a saddle joint. It is the measurement and characterization of this complex motion of the thumb which constitutes the substance of this invention.

Relevant Literature

"Telepresence Master Glove Controller for Dexterous Robotic End-effectors," Scott S. Fisher, SPIE Vol. 726, Intelligent Robots and Computer Vision: Fifth in a Series (1986), pp. 396–401, provides a glove with flex sensors and an electromagnetic position sensor. U.S. Pat. No. 4,988,981 provides a glove with flex sensors and a position sensor. U.S. Pat. Nos. 5,047,952 and 5,280,265 provide a glove with variable-resistance strain-sensing flex-sensors. The Cyber-Glove™ User's Manual provides a previous simple description of a thumb model using thumb abduction and thumb rotation sensors.

SUMMARY OF THE INVENTION

The subject invention provides a method for using the output values from two sensors, typically bend sensors referred to as the thumb abduction (TA) and thumb rotation (TR) sensors, to generate an accurate approximation of the motion of the thumb about the trapeziometacarpal (TM) joint.

DESCRIPTION OF THE SPECIFIC EMBODIMENTS

In accordance with the subject invention, methods and systems are provided for determining the position of a thumb which offer distinct advantages over known prior-art arrangements. The subject invention provides means whereby measurements from two goniometers placed conveniently about a hand may be used to accurately determine the complex structure of the thumb trapeziometacarpal joint. The position and orientation of the thumb or portions thereof may be determined relative to a reference coordinate system. By using further goniometers, the placement of the entire thumb and other fingers and joints of the hand may be determined.

Briefly, the subject invention provides for two modeled trapeziometacarpal joint (TMJ) axes. The first axis is referred to as the roll axis (TMJR) and its position predefined, as will be described later. The position of the second TMJ axis, which axis shall be referred to as the pitch axis (TMJP), is determined using measurements of the thumb abduction (TA) and thumb rotation (TR) and the angles of rotation of the thumb about each of these two TMJ axes. The position of any point on the thumb may then be determined by designating that the thumb metacarpophalangeal joint (thumb MPJ) and thumb interphalangeal joint (IJ) axes are parallel to the calculated TMJP axis, employing the values obtained from goniometers used to measure the thumb MPJ and IJ angles, and using an anatomical model of the skin and tissue placement about the bones on the hand and thumb.

Figure 1:
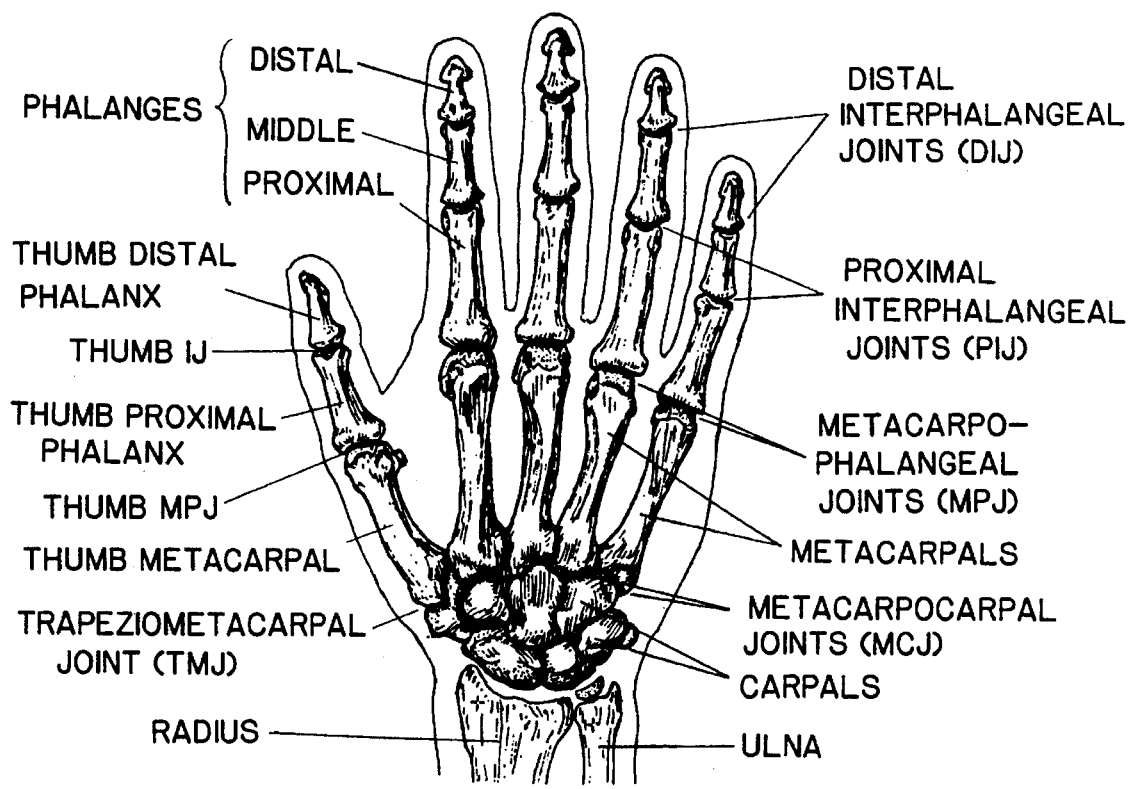
FIG. 1 is an anatomical description of the human hand.

Referring now to the drawings, FIG. 1 provides the anatomical definitions of the various joints and bones of a hand and wrist. These definitions will be used throughout the subject specification and claims.

Figure 2:
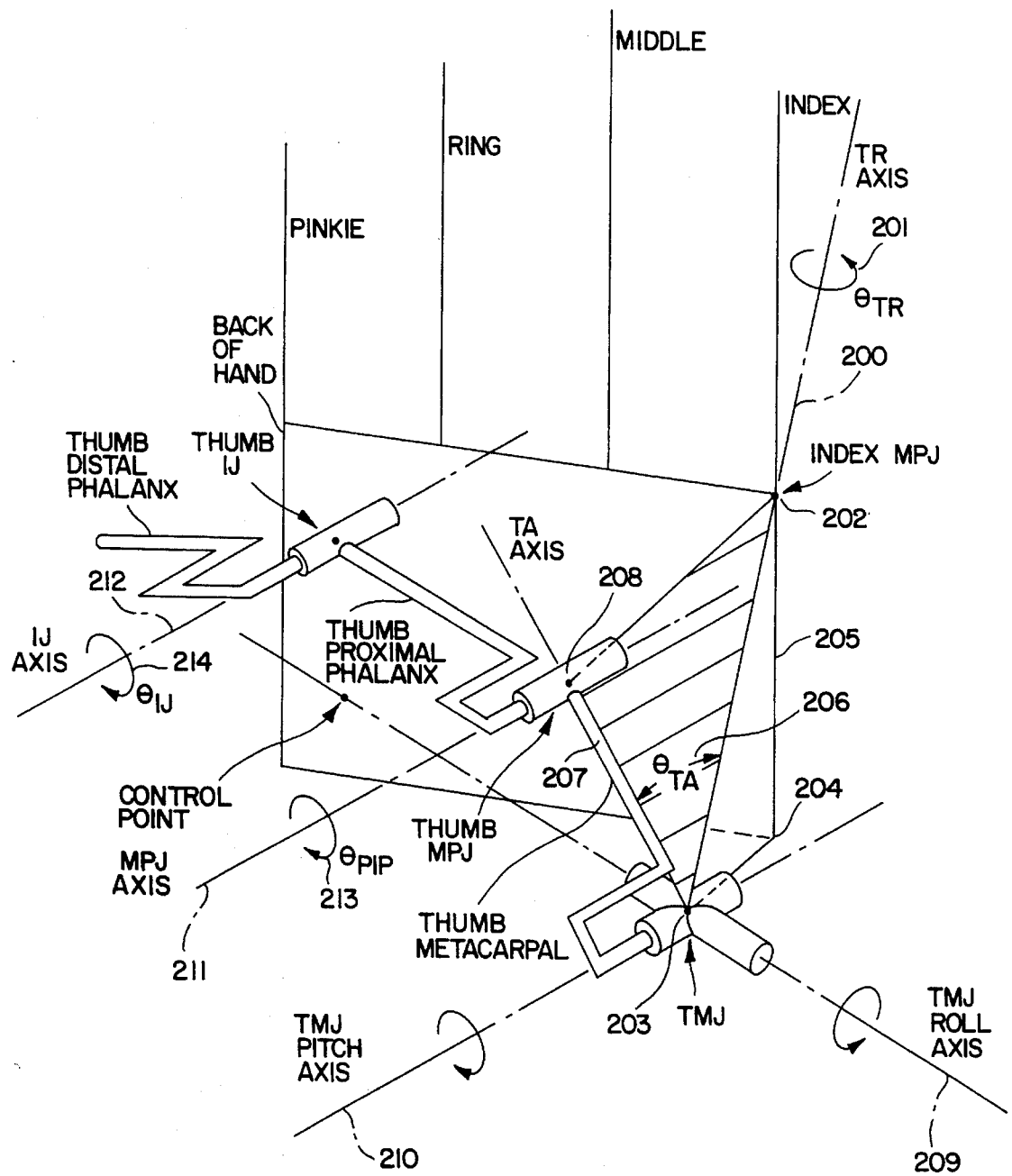
FIG. 2 is a model of a thumb, indicating the various axes.

FIG. 2 provides the joint-link geometry used throughout the subject specification and claims to model the joint articulations and bones defined in FIG. 1, as well as their related motions. The term "link" is used to refer to a physical bone, often a phalanx, or a modeled interconnect between two joints. Joints of the hand as shown anatomically in FIG. 1 are modeled using one or more single-axis hinged joints as shown in FIG. 2. Each modeled joint is shown schematically in FIG. 2 as a cylinder comprising an outer cylindrical casing and an inner cylindrical rod capable of rotating relative to the outer casing about a single axis. The outer casing is affixed to a first link and the inner cylinder is rigidly affixed to a second link. If a physical joint of the hand, such as the TMJ, has more than one possible articulation, the model of FIG. 2 provides for multiple cylindrical joints and axes to be located at the same point but with different orientations. Where such multiple-axis joints are used, each joint of the multiple joint is assumed to be infinitesimally small such that the axes of each individual joint making up the multiple joint intersect at a single point.

For the purposes of the calculations we must determine a relationship between a value taken directly from the sensor and the angle which is to be used by the hand model. To this end, we define an initial spatial conformation of the hand for which all angles and positions of the joints are known. Each initial angle is measured relative to its related reference angle. The initial position of each joint is measured relative to reference coordinate system. An initial joint angle value relative to this conformation is known along with a corresponding sensor value. The initial position of each link corresponding to the initial sensor values may be used to aid in determining the initial joint angle values. The term "initial value∞" shall be used to refer to one or more of (a) an initial joint angle value (e.g., degrees or radians), (b) an initial link position (e.g., centimeters or inches), (c) an initial sensor value (e.g., "least significant bits" from an analog-to-digital converter (ADC), where the value is called the A/D value; or volts).

Typically, when a goniometer is used to measure a joint angle, its output, often just a number from an ADC, must be calibrated to represent a physical angle of the hand in degrees or radians. To accomplish the calibration, a gain parameter may be used as provided by the following equation:

$$\text{Angle}-\text{Angle\_initial}=\text{Gain}*(\text{Sensor\_value}-\text{Sensor\_value\_(Initial)})$$

where:
(a) Sensor_value is the sensor output at an arbitrary time;
(b) Sensor_value_initial is the initial sensor value known to correspond to Angle_initial;
(c) $\text{Angle}_{13}$ initial is the initial joint angle;
(d) Angle is the calibrated angle corresponding to the instantaneous value of Sensor_value;
(e) Gain is a parameter used to convert the range of Sensor_values to the appropriate range of Angles.

Figure 5:
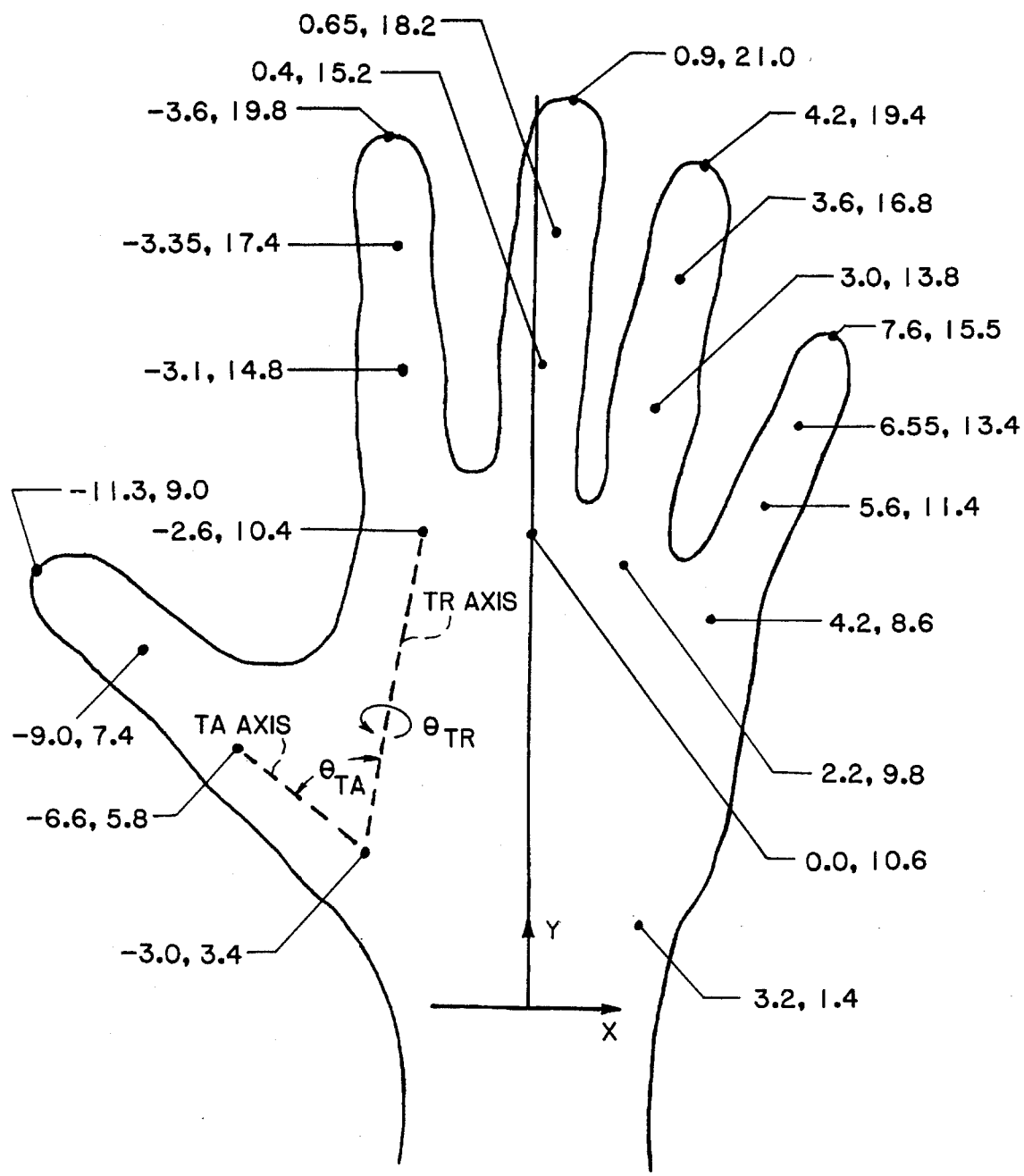
FIG. 5 provides a traced physical hand with various joint locations labeled with x and y coordinates as provided in Table 1.
Figure 6:
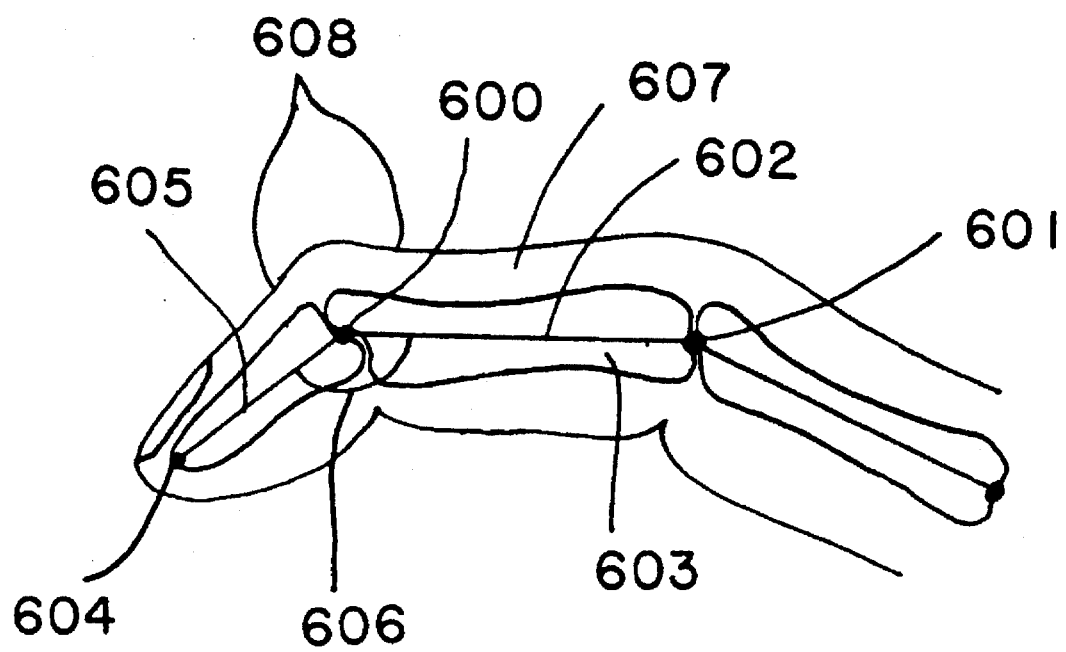
FIG. 6 depicts a longitudinal cross-section of a finger for relating physical joints, bones and surrounding tissue with the modeled joints and links.

Determination of suitable values for Angle_initial for each joint may be aided by photocopying a physical hand in a first fully-specified handshape (e.g., flat) onto a piece of graph paper, and by measuring finger diameters and the other dimensions of the hand necessary for the calculations of the initial values. With the physical hand in the specified geometric shape, the value of Angle_initial may be determined for each joint. A goniometer output for a particular joint, when the hand is in this handshape, is then selected as the Sensor_value initial for that joint. To set the value of Gain, a second specified handshape is needed. With the physical hand in this second specified handshape, the value of each joint angle Gain is adjusted until the corresponding modeled joint produces a sufficiently matching angle. Table 1 provides a typical hand geometry file. FIG. 5 provides a traced physical hand with various joint locations labeled with x and y coordinates as provided in Table 1. Table 2 provides a typical calibration file, where the column labeled "offset" is equivalent to Sensor_value_initial as defined above.

TABLE 1

3D HAND GEOMETRY follows:
! ==
! NOTE
!     The geometry of the system axes is to change in
!     in future releases to account for the roll of the arm
!     to equate to roll of about the X-axis. The Y-axis
!     will then be through the wrist from right to left.
!     The Z-axis will always be up.
! ==
! This geometry is for a:
RIGHT HAND.
!     The handedness can be changed by flipping the geometry

TABLE 1-continued

```
!       across its axis of symmetry.
!         *Currently this is { x = -x }, but it will be { y = -y }
!           with the X-axis an the axis of symmetry.
!    =
!    backbone of hand -- flat structural geometry (centimeters)
!    =
!           wrist_offset = offset of wrist's center of rotation
!             x       y        z relative to tracker receiver.
           0.00    6.00    -2.00
!    =
!    # of fingers, # of vertices/finger, thumb-aspect and hand-roll
!           thumb-roll = roll angle of thumb interphalangeal bend axis
!           hand-roll = roll angle of wrist pitch axis
!         in degrees relative to plane of metacarpals.
           5       4     45.00  11.00
!    =
!    Each finger is with <x, y, z> joint/tip position relative to
!       the plane of the metacarpals (unrolled) with origin-wrist
!       the initial integer is currently used as a VGA color reference
!       the fourth real is the finger diameter at the joint.
!    Thumb
1
        -3.00   3.40   -1.00   1.80
        -6.60   5.80   -0.50   1.40
        -9.00   7.40   -0.50   1.20
       -11.30   9.00   -0.50   0.90
!    Index
1
        -2.60  10.40    0.00   1.30
        -3.10  14.80    0.00   1.20
        -3.35  17.40    0.00   1.00
        -3.60  19.80    0.00   0.80
!    Middle
1
         0.00  10.60    0.00   1.20
         0.40  15.20    0.00   1.10
         0.65  18.20    0.00   0.90
         0.90  21.00    0.00   0.80
!    Ring
1
         2.20   9.80    0.00   1.00
         3.00  13.80    0.00   1.00
         3.60  16.80    0.00   0.90
         4.20  19.40    0.00   0.80
!    Pinky
1
         4.20   8.60    0.00   1.00
         5.60  11.40    0.00   1.00
         6.55  13.40    0.00   0.90
         7.60  15.50    0.00   0.70
!    =
!    There will be several parameters describing the
!       carpals. Presently only one point is used.
!    pisiform carpal bone = the bone that the hand rests on
         3.20   1.40   -2.00
!    =
!    radial-carpus, ulna-carpus at the wrist joint
!    radial-cranon, olecranon, and ulna-coronoid points at elbow joint
        -3.00    0.00    0.00
         3.00   -0.50    2.00
        -3.70  -30.00    0.50
         0.00  -29.50   -2.00
         4.50  -29.00    2.50
!    Thumb roll axis. This is the vector the thumb rolls about as it abducts
!    and rotates about the MCP joint
!    Fairly good results are had just using the vector from the thumb MCP
!       joint to the pinky MCP joint
         7.00    3.00   -2.00
!    MCP rotation axis. Nominally the vector from the thumb MCP joint to the index
!    finger MCP joint
         0.40    7.00    1.00
```

TABLE 2

```
VHv2.0.2
!    Virtex CyberGlove ™ -> Virtual Hand calibration file
!    = Virtual Hand Software 2.0.2 =
!
```

TABLE 2-continued

```
GLOVE CALIBRATION follows:
!  joint, offset, gain, gesture
       FINGER 0:
             0      73      0.01553    0
             1     109      0.01255    0
             2     105      0.01584    0
             3      69      0.00580    0
       FINGER 1:
             0      85      0.01867    0
             1      77      0.01616    0
             2      65      0.00753    0
             3     125      0.00449    0
       FINGER 2:
             0      79      0.02039    0
             1      69      0.01647    0
             2      91      0.01051    0
             3     125      0.24800    0
       FINGER 3:
             0      85      0.02102    0
             1      72      0.01741    0
             2      81      0.01051    0
             3     145      0.00612    0
       FINGER 4:
             0      85      0.01898    0
             1      65      0.01757    0
             2     101      0.00988    0
             3     121      0.00596    0
       FINGER 5:
             0      71      0.00910    0
             1     145      0.01239    0
             2      81      0.00659    0
             3      60      0.00781    0
!  E_O_CAL
TRACKER CALIBRATION follows:
!  x, y, z, azimuth, elevation, roll
   20.00  −40.00   10.00  0.00  0.00  0.00
!  E_O_CAL
!
```

Typically, goniometer measurements, and optionally other types of sensor measurements, are assumed to be in the form of numbers, often derived from an ADC. In the case where an optical encoder is used to measure joint angle, the values might be numbers where no ADC was used. However, the procedure for determining thumb and hand position as specified in the subject application does not depend on the use of digital values. The sensor values may also be processed in analog form, such as voltage, provided appropriate analog signal processing means.

Figure 3:
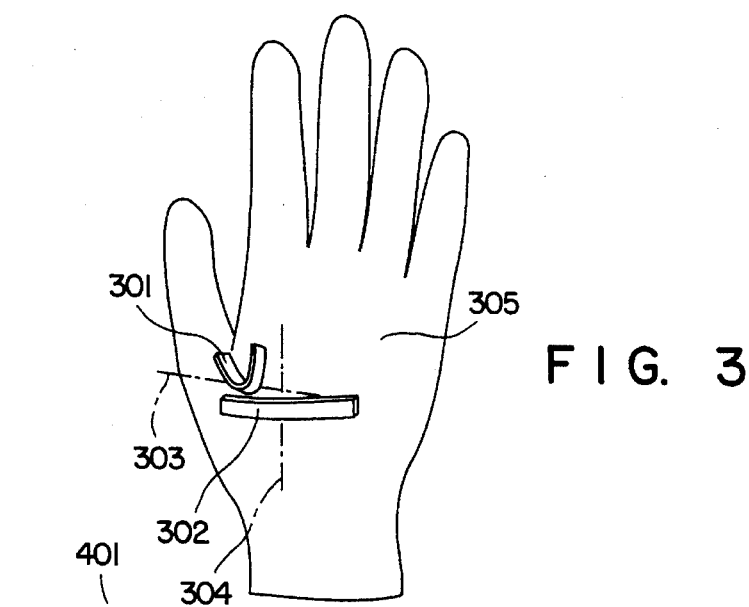
FIG. 3 shows the typical location of a TA and TR bend sensor on a hand or glove-like support.

Referring now to FIGS. 2 and 3, a first goniometer 302 is employed to measure an angle $\theta_{TR}$ 201 about an axis 200 (in FIG. 3, 304), referred to as the thumb rotation (TR) axis. For simplifying the calculations, the TR axis is defined as passing through the index finger metacarpophalangeal joint (index MPJ) 202 and the TMJ 203. An alternative, which requires less convenient calculations, is to define the TR axis as passing through the index MPJ 202 and the metacarpocarpal joint of the index finger 204, i.e. the TR axis is coaxial with the index metacarpal 205 (see also FIG. 1). When the goniometers used are a type of flexible bend sensor (flex sensor), i.e., sensors where the output varies as the sensors are bent, the first goniometer 302 is conveniently about 1.5" in length and is positioned normal to the TR axis as defined above, and positioned over the index metacarpal, extending approximately 0.75" to each side.

A second goniometer 301 is employed for measuring thumb abduction, defined as the angle $\theta_{TA}$ 206 between the thumb metacarpal 207 and the TR axis 200 (or alternately, 205). The TA axis about which $\theta_{TA}$ is measured is the axis normal to the plane defined by the thumb metacarpal and the TR axis (in FIG. 3, 303). Obviously, as defined, when the thumb metacarpal is moved, the TA axis varies accordingly.

When the goniometer used is a single-axis-measuring flex sensor, the TA goniometer 301 is positioned pre-flexed in a "U" shape on the soft tissue between the thumb and index metacarpals. Positioned as such, the TA axis 303 is normal to the surface of the hand and $\theta_{TA}$ is related to the size of the opening of the "U".

Figure 7A:
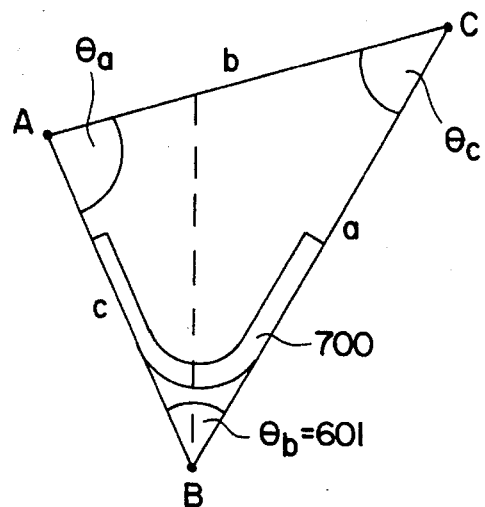
FIGS. 7A–7C provide schematics of different locations and arrangements of a thumb abduction sensor used to measure the thumb abduction angle.
Figure 7B:
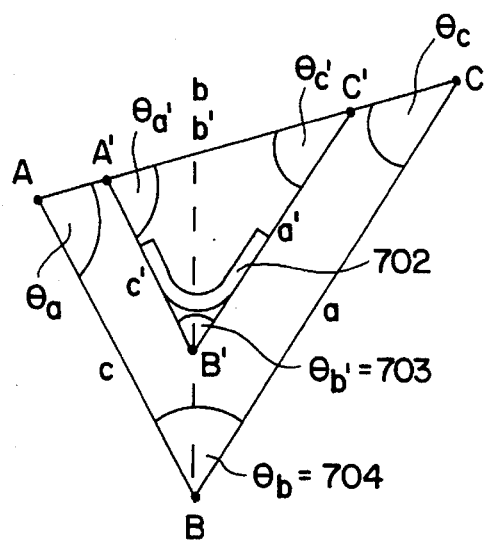
Figure 7C:
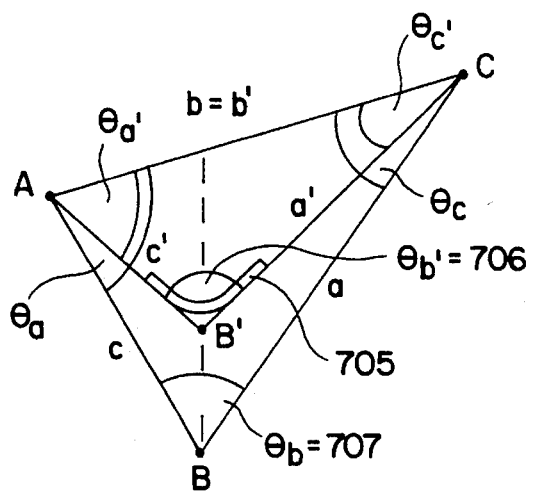

FIG. 7A shows one placement of a TA sensor 700 relative to points A (thumb MPJ), B (TMJ) and C (index MPJ). The tangents of the sensor are shown tangent to sides a and c of the triangle. In this case, the sensor measures the desired $\theta_{TA}$ 601. FIG. 7B shows another placement of TA sensor 702 which, as shown using similar triangles, also measures the desired $\theta_{TA}$ 704. FIG. 7C shows an arrangement where TA sensor 705 will provide a signal related to $\theta_{TA}$ by the following equation 2:

$$\theta_{TA} = \arccos\{[(a^2+c'^2-a^2-c^2)-2a'c'*\cos(\theta_{TA\_MEASURED})]/-2ac\},$$

where $\theta_{TA\_MEASURED}$=706 and $\theta_{TA}$=707.

Knowing the position of the TR axis and the angles $\theta_{TR}$ and $\theta_{TA}$, as determined using equation (1) and the Sensor_ values of the TR and TA goniometers, the position of the thumb metacarpophalangeal joint (thumb MPJ) 208 may be determined. From $\theta_{TR}$ and $\theta_{TA}$, $\Delta\theta_{TR}$ and $\Delta\theta_{TA}$ are calculated as the angle differences of $\theta_{TR}$ and $\theta_{TA}$ from their respective Angle_initial values. The first initial handshape defines the initial TA axis, typically as normal to the plane of the initial thumb metacarpal and the TR axis. One method of determining the position of the thumb MPJ is to rotate the initial thumb MPJ position about the initial TA axis by amount $\theta_{TA}$ to produce a first rotated thumb MPJ position. This first rotated thumb MPJ position is then rotated about the fixed TR axis by an amount $\Delta\theta_{TR}$ to produce a second rotated thumb MPJ position. A second method of determining the position of the thumb MPJ is to first rotate the initial thumb MPJ position about the TR axis by $\Delta\theta_{TR}$ to produce a third rotated thumb MPJ position and a rotated TA axis. This third rotated thumb MPJ position is then rotated by $\Delta\theta_{TA}$ about the rotated TA axis to produce a rotated thumb MPJ position equivalent to the second rotated thumb MPJ position.

Using the second rotated thumb MPJ position and the TMJ, along with the TMJ roll axis 209, we can determine the TMJ pitch axis 210. In the drawing, the TMJR axis is predefined as passing through the TMJ 203 and a point projected normally outward from the metacarpus, nominally 2 cm from the palmar side of the ring metacarpophalangeal joint. This axis may be further optimized by varying the spatial location of the point about the nominal location and observing the effect on the accuracy of the correspondence between the physical thumb and the thumb model. Using the TMJ and the second rotated thumb MPJ position, the thumb metacarpal axis 207 is determined. Using known mathematical vector cross-product techniques, axis 207 is crossed into the TMJR axis to yield the TMJ pitch axis 210.

The thumb MPJ axis 211 and the IJ axis 212 are designated as parallel to the calculated TMJP axis 210. The angles measured about the thumb MPJ and IJ axes are defined as $\theta_{MPJ}$ 213 and $\theta_{IJ}$ 214. By employing further goniometers to measure the changes in angles from the initial values of the thumb $\theta_{MPJ}$ and $O\theta_{IJ}$, designated as $\Delta\theta_{MPJ}$ and $\Delta\theta_{IJ}$, respectively, we may calculate and completely characterize the kinematic positioning of the bony structure of the thumb. When a flex sensor is used as the goniometer for the thumb MPJ and IJ, it is conveniently placed across the surface of the joint. When the kinematic positioning of the bony structure of the thumb is used in conjunction with an anatomical model of the skin and tissue of the hand and thumb, the position of any point about the hand and thumb may be determined.

Figure 4A:
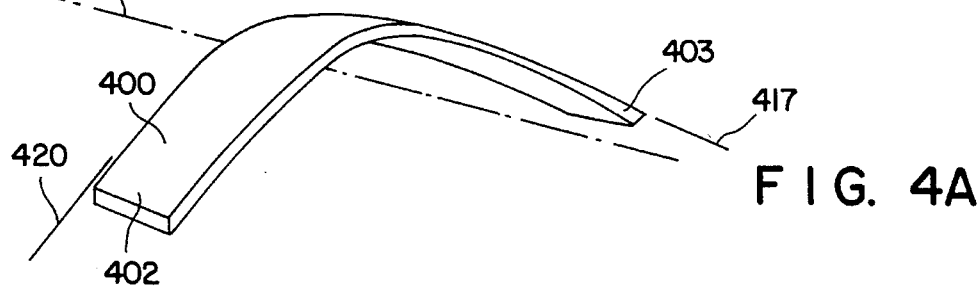
FIG. 4A provides a typical flexible bend sensor.
Figure 4B:
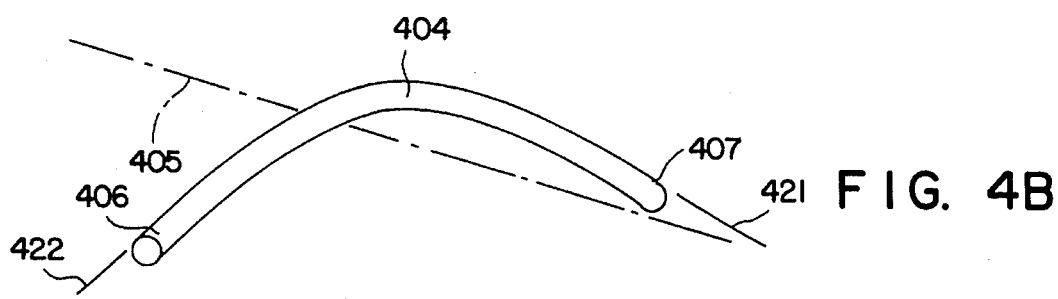
FIG. 4B provides a fiber-optic bend sensor.
Figure 4C:
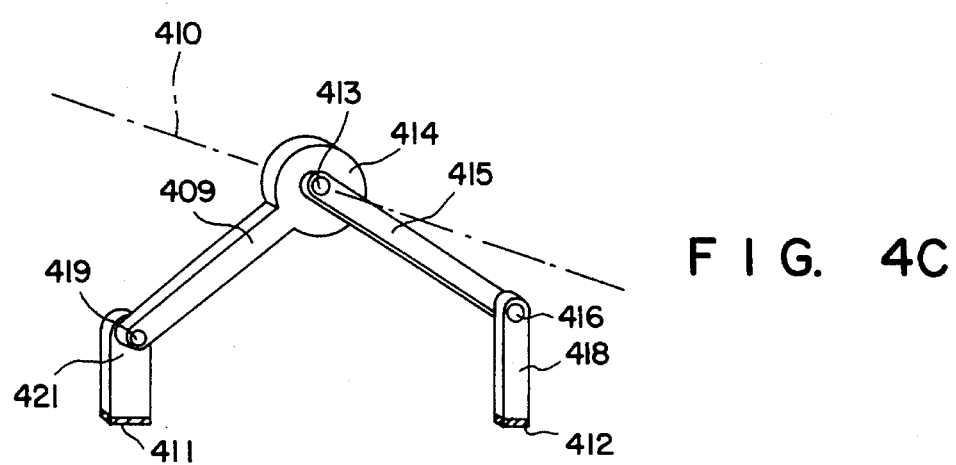
FIG. 4C provides a goniometer where a potentiometer-like rotation sensing device is used to measure angle at one or more hinged articulations.

Referring now to FIGS. 4A–4C, a number of different goniometers are depicted. FIG. 4A, provides a typical flex sensor 400. A flex sensor which often takes this form is a variable resistance strain sensing goniometer such as is described in U.S. Pat. Nos. 5,047,952 and 5,280,265. These patents are incorporated by reference as describing a glove and sensors finding particular application in combination with the subject invention. Such a structure provides a sensor with a low profile, high degree of flexibility and largely a single axis of flexure. The sensor measures the angle between the tangents 417 and 420 to the end portions of the sensors 403 and 402 respectively, and the sensor output is largely independent of the location of axis 401 about which the sensor is bent and the associated radius of curvature of the bend. Such a flex sensor is typically placed in and allowed to slide in a guiding element, such as a pocket, where the guide is affixed over a human joint or otherwise articulated structure. Frequently, the human joint is a knuckle of the hand or a wrist joint and the sensors are placed in guiding pockets in a glove-like support.

FIG. 4B provides another common flex sensor 404. A sensor which often takes this form is a light tube or fiber optic bend sensor such as is described in U.S. Pat. Nos. 4,414,537 and 4,542,291. One disadvantage of this type of structure is that its bend is not mechanically constrained to be largely about a single axis 405. The output signal from such a sensor typically depends on radius of curvature as well as actual angle between the tangents 421 and 422 at the ends 407 and 406 of the sensor respectively. Typically, such a sensor is held in juxtaposition to a human joint or otherwise articulated structure by tubular guides affixed on either sides of the axis of articulation, where the sensor is allowed to slide relative to the guide. Frequently, the human joint is a knuckle of the hand or a wrist joint and the sensors are guided along a glove-like support.

The goniometer of FIG. 4C includes a type of rotary angle sensor with body 414, axle 413 and axis of rotation 410. The body 414 is typically affixed by member 409 to member 421 by a axle 419. Member 421 may then affixed by end 411 to a portion of the structure which angle is to be determined. Similarly, axle 413 is typically rigidly affixed to member 415 which is connected to member 418 by axle 418. Member 418 may then be affixed by end 412 to a second portion of the structure capable of articulating relative to the first portion. As the first portion of the structure in question moves relative to the second portion, the value of the rotary angle sensor changes accordingly in relation to the amount of movement. Typical rotary angle sensors include rotary Hall Effect sensors, optical encoders, RVDT's (Rotary Variable Differential Transformers), and the like. Typically, such a goniometer is held in juxtaposition to a human joint or otherwise articulated structure by affixing ends 411 and 412 to either side of the axis of articulation by Velcro or other strapping methods. Frequently, the human joint is a knuckle of the hand or a wrist joint and the goniometers are strapped around the finger or wrist by a Velcro strap. The goniometers may also be affixed to a glove-like support or other fitted covering.

A fitted covering over all or a portion of the hand may be employed, where the fitted covering may serve as a support for one or more goniometers that measure the position of one or more of the other fingers in addition to the thumb. One may wish to determine the position of the index finger or other fingers in conjunction with the thumb, as previously described in the Background. For example, the combination of thumb and index finger can be used as tongs for a variety of manipulations.

Any publication or patent described in the specification is hereby included by reference as if completely set forth in the specification.

While the invention has been described with reference to specific embodiments, various modifications and amplifications may occur to those skilled in the art without departing form the true spirit and scope of the invention as defined by the appended claims.

What is claimed is:

1. A method employing sensors, a data processor and a memory for measuring the position of an anatomical model of at least a portion of a thumb relative to a reference coordinate system, wherein said anatomical model comprises joints and links, wherein each joint is a revolute joint and the axis of each joint represents the center of rotation between two articulated bone segments and each bone segment is represented by a link, said measuring using said anatomical model employing at least some of the following components: (1) a thumb rotation axis (TR axis) and the angle about said axis, $\theta_{TR}$; (2) a trapeziometacarpal joint, TMJ, comprising a pitch axis (TMJP) and a roll axis (TMJR); (3) a thumb metacarpal; (4) a thumb proximal phalanx; (5) a thumb distal phalanx; (6) a thumb metacarpophalangeal joint (thumb MPJ); (7) an interphalangeal joint (IJ); (8) a thumb abduction axis (TA axis) and the angle about said TA axis, $\theta_{TA}$, said TA axis normal to the plane defined by (a) the thumb metacarpal and (b) the TR axis; (9) an index metacarpophalangeal joint (index MPJ), wherein each of said components has a known initial value for an initial thumb position; said method comprising:

transmitting signals to said data processor from said sensors mounted in juxataposition to said thumb, wherein said signals indicate the change in values, $\Delta\theta_{TR}$ and $\Delta\theta_{TA}$, for $\theta_{TR}$ and $\theta_{TA}$ from said initial values defining the movement of the thumb from said initial position;

processing said signals in said memory relating to said $\Delta\theta_{TR}$ and $\Delta\theta_{TA}$, by first rotating said initial position of said thumb MPJ about the initial TA axis by an amount $\Delta\theta_{TA}$ to determine a first rotated thumb MPJ; and further rotating said first rotated thumb MPJ about the TR axis by an amount $\Delta\theta_{TR}$ to produce a signal related to a second rotated thumb MPJ;

processing said signal related to a second rotated thumb MPJ in conjunction with said thumb TMJ to define the position of said thumb metacarpal;

relating the position of said TMJP axis as being normal to the plane defined by said thumb metacarpal and said TMJR axis to specify the orientation of said thumb metacarpal;

whereby the position and orientation of said thumb metacarpal relative to a reference coordinate system is determined.

2. A method according to claim 1, further comprising the steps of:

transmitting signals from sensors mounted in juxataposition to said thumb, wherein said signals indicate the change in values, $\Delta\theta_{MPJ}$ and $\Delta\theta_{IJ}$, for $\theta_{MPJ}$ and $\theta_{IJ}$ joint angles about the axes of said thumb MPJ and IJ, respectively;

processing said signals in said memory for said $\Delta\theta_{MPJ}$ and $\Delta\theta_{IJ}$ joint angles, in conjunction with said thumb MPJ and IJ axes set parallel to said TMJP axis, whereby said thumb proximal phalanx is rotated by $\Delta\theta_{MPJ}$ about said thumb MPJ axis relative to the position of said thumb metacarpal, and said distal phalanx is rotated by $\Delta\theta_{IJ}$ about said IJ axis relative to said rotated proximal phalanx;

whereby the position of said thumb proximal and/or distal phalanges relative to said thumb metacarpal is determined.

3. A method according to claim 2, further comprising calculating the position of a point of said anatomical model of said thumb by means of the dimensions of said anatomical model of said thumb and the position of said links of said model.

4. A method according to claim 1, wherein said TR axis is defined as passing through said TMJ and said index MPJ.

5. A method according to claim 1, wherein said components further include a ring metacarpophalangeal joint, and said TMJR axis is defined as passing through said TMJ and a point which is optimized about a nominal location approximately 2 cm from the palmar side of said ring metacarpophalangeal joint.

6. A method according to claim 1, wherein said components further include as additional components the wrist or one or more phalanges of one or more fingers of the hand and further calculating the position of said additional components.

7. A system for measuring the position of at least a portion of a thumb, using an anatomical model employing: (1) a thumb rotation axis (TR axis) and the angle about said axis, $\theta_{TR}$; (2) a trapeziometacarpal joint, TMJ, comprising a pitch axis (TMJP) and a roll axis (TMJR); (3) a thumb metacarpal; (4) a thumb proximal phalanx; (5) a thumb distal phalanx; (6) a thumb metacarpophalangeal joint (thumb MPJ); (7) an interphalangeal joint (IJ); (8) a thumb abduction axis (TA axis) and the angle about said TA axis, $\theta_{TA}$, said TA axis normal to the plane defined by (a) the thumb metacarpal and (b) the TR axis; (9) an index metacarpophalangeal joint (index MPJ); and (10) an index metacarpal, wherein the change in angles of $\theta_{TR}$ and $\theta_{TA}$ from known initial values for an initial thumb position as a result of movement of said thumb are $\Delta\theta_{TR}$ and $\Delta\theta_{TA}$, respectively, said system comprising:

a first goniometer in juxtaposition to the soft tissue between said thumb metacarpal and said TR axis to provide a signal for $\theta_{TA}$ indicating said $\Delta\theta_{TA}$ value;

a second goniometer in juxtaposition to said TR axis to provide a signal for $\theta_{TR}$ indicating said $\Delta\theta_{TR}$ value;

means for supporting said goniometers in position in relation to the thumb;

a data processor for receiving said signals and processing said signals to provide a value for the position of said thumb metacarpal from said $\Delta\theta_{TA}$ and $\Delta\theta_{TR}$ values; and a data processor for receiving said value for the position of said thumb metacarpal for determining the orientation of said thumb metacarpal from said value of the position of said thumb metacarpal and the position of said TMJP axis as being normal to the plane defined by said thumb metacarpal and said TMJR axis.

8. A system according to claim 7, wherein said supporting means comprises a fitted covering over at least a portion of said thumb and index finger.

9. A system according to claim 8, wherein said supporting means further comprises a fitted covering over the remaining fingers of a hand, and further including at least one goniometer supported by said fitted covering for measuring the position of at least one of said fingers.

10. A system according to claim 7, said components further comprising a metacarpus, wherein said second goniometer measures an angle between a first point on said metacarpus and a second point on said thumb metacarpal or on the tissue between said thumb metacarpal and said TR axis.

11. A system according to claim 7, further comprising:

a third goniometer in juxtaposition to said thumb metacarpophalangeal joint to provide a signal $\theta_{MPJ}$ indicating $\Delta\theta_{MPJ}$, the change in the angle about the axis of said thumb MPJ;

a fourth goniometer in juxtaposition to said thumb interphalangeal joint to provide a signal $\theta_{IJ}$ indicating $\Delta\theta_{IJ}$, the change in the angle about the axis of said IJ;

a data processor for receiving and processing said signals to determine the position of said proximal and distal phalanges using said $\Delta\theta_{MPJ}$ and $\Delta\theta_{IJ}$ joint angles, in conjunction with the position of said thumb MPJ and where said thumb MPJ and IJ axes are set parallel to said TMJP axis.

* * * * *